US00PP17081P2

(12) United States Plant Patent
Lemon

(10) Patent No.: US PP17,081 P2
(45) Date of Patent: Sep. 5, 2006

(54) ***GERANIUM* PLANT NAMED 'ELEGANCE LIGHTLAVENDER SPLASH'**

(50) Latin Name: *Pelargonium domesticum*
Varietal Denomination: Elegance LightLavender Splash

(75) Inventor: David G. Lemon, Lompoc, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 11/177,685

(22) Filed: Jul. 8, 2005

(51) Int. Cl.
*A01H 5/00* (2006.01)

(52) U.S. Cl. ..... Plt./331

(58) Field of Classification Search ..... Plt./331
See application file for complete search history.

*Primary Examiner*—Kent Bell
(74) *Attorney, Agent, or Firm*—The Webb Law Firm

(57) ABSTRACT

'Elegance LightLavender Splash' is a new variety of *geranium* having large flowers and lavender petals with dark red-purple eyes.

1 Drawing Sheet

Botanical classification: *Pelargonium domesticum.*
Varietal denomination: 'Elegance LightLavender Splash'.

BACKGROUND OF THE INVENTION

The present invention comprises a new and distinct cultivar of *Pelargonium domesticum* known by the varietal name 'Elegance LightLavender Splash'. The new variety was discovered in Lompoc, Calif. The new variety is a result of cross breeding Light Pink Seedling #4373 (female parent) (unpatented) and Lavender Seedling #3020 (male parent) (unpatented). The purpose of the breeding program was to introduce new regal *geraniums* that are less sensitive to light and temperature. The new variety is similar in plant type to its female parent, but differs in flower color. Conversely, the new variety is similar in flower color to its male parent, but differs in plant type. 'Elegance LightLavender Splash' is more compact, with earlier and lighter colored flowers than 'Elegance Lavender' (U.S. Provisional patent application Ser. No. 60/603,817). 'Elegance LightLavender Splash' is also very free flowering, has a good response to extra light, and exhibits larger flowers when compared to other varieties known to the breeder. The new variety was first asexually reproduced by cuttings in Connellsville, Pa. The new variety has been trial and field tested and has been found to retain its distinctive characteristics and remain true to type through successive propagations.

The new variety was grown in a glass greenhouse in a 4" pot in Connellsville, Pa. in a soilless media with constant fertilizer at 200 ppm nitrogen and potassium. The new variety was grown under 16-hour days with supplemental high pressure sodium lamps. The new variety exhibits developed roots at 14 days at an average temperature of 21° C. and has a response time of fifteen weeks from a rooted cutting to flowering in a 12.7 cm. container.

DESCRIPTION OF THE DRAWING

The accompanying photographic drawing illustrates the new variety, with the color being as nearly true as is possible with color illustrations of this type.

DESCRIPTION OF THE PLANT

Figure 1:
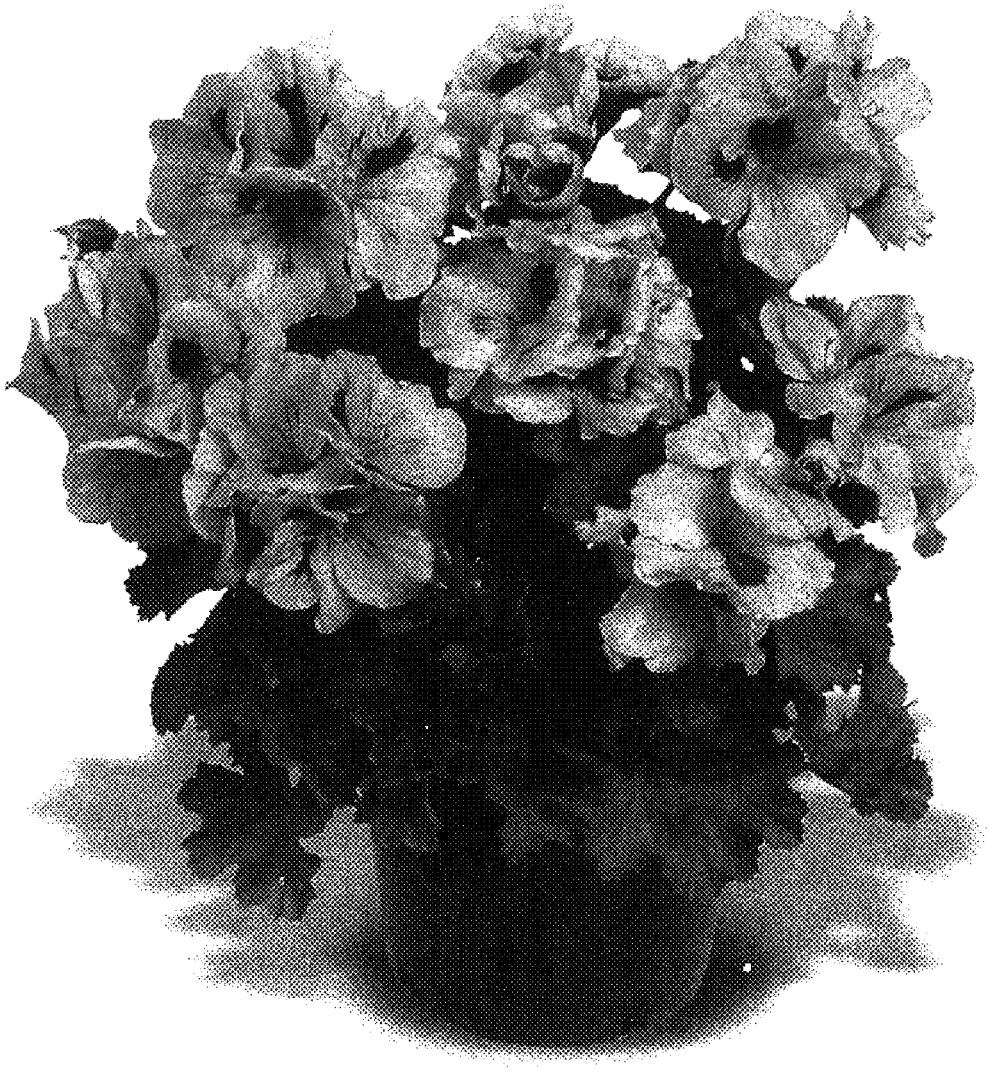

The following detailed description sets forth the characteristics of the new cultivar. The data which defines these characteristics were collected by asexual reproductions carried out in Connellsville, Pa. The color readings were taken indoors under 65–85 foot candles of cool white fluorescent light. The new variety was eight weeks from a rooted cutting when described. Color references are primarily to the 1966 R.H.S. Colour Chart of The Royal Horticultural Society of London.

PLANT

Market class: Regal.
Time to initiate roots: About 9 days at about 21° C.
Time to develop roots (days, temperature): About 14 days at about 21° C.
Time to produce a finished flowering plant from a rooted cutting: About 15 weeks in a 12.7 cm. container.
Rooting habit: Good to excellent.
Form: Round-mounded.
Height from media surface to top of foliage: 19.0–21.0 cm.
Height from media surface to top of flowers: 27.0–29.0 cm.
Plant diameter: 21.0–23.0 cm.
Strength: No artificial support is needed.
Branching habit: Free basal branching.
Stem:
- *Main stem length.*—12–14 cm.
- *Diameter.*—1.2–1.5 cm.
- *Color.*—Yellow-Green Group 144A.
- *Texture.*—Leathery texture.
- *Pubescence.*—Moderate.
- *Internode length.*—1.0–1.5 cm.

Lateral branches:
- *Length.*—Primary: 9.5–12.0 cm. Secondary: Plant is too young to measure.
- *Diameter.*—Primary: 0.5–1.0 cm. Secondary: Plant is too young to measure.
- *Internode length.*—1.5–3.0 cm.
- *Texture.*—Leathery.
- *Pubescence.*—Moderate.
- *Color.*—Yellow-Green Group 144A.

Foliage:
*Arrangement.*—Alternate with a stalked leaf attachment.
*Stipules.*—Size: 4.0–5.0 cm. Color: Yellow-Green Group 143A.
*Zone.*—Not present.
*Size of leaf.*—Length: 4.0–7.0 cm. Width: 6.0–11.0 cm.
*Shape of leaf* (*generally*).—Reniform.
*Shape of apex.*—Pointed, jagged.
*Shape of base.*—Truncate.
*Texture.*—Smooth upper surface and leathery.
*Margin type.*—Serrated, lobed.
*Pubescence.*—Upper surface: None. Lower surface: Slight.
*Color.*—Young leaves: Upper surface: Green Group 137B. Lower surface: Green Group 138B. Mature leaves: Upper surface: Green Group 137A. Lower surface: Green Group 138A.
*Petiole.*—Length: 3.0–7.0 cm. Diameter: 2.0–3.0 cm. Color: Green Group 143A.
*Veins.*—Venation type: Branched; palmate. Color: Upper surface: Green Group 137B. Lower surface: Green Group 138B.

INFLORESCENCE

Bud:
*Stage of development when bud characteristics determined.*—Just prior to sepals parting at tips.
*Shape of cluster.*—Elliptical when no color is showing.
*Diameter of cluster.*—2.0–2.5 cm.
*Number of buds per cluster.*—6.
*Shape of individual bud.*—Elliptical or oval when no color is showing.
*Length of individual bud.*—1.5–2.0 cm.
*Width of individual bud.*—0.5–1.0 cm.
Natural flowering season at specified locations: Would naturally flower under cooler temperatures in California; requires cool temperatures and light to flower fully in the greenhouse after buds are set.
Blooming habit: Requires approximately 10 weeks under specific greenhouse temperature and light regimes to set bud.
Umbel diameter: 10.5–11.0 cm.
Umbel depth: 6.5 cm.
Borne: Umbel, flowers on pedicel, pedicel on peduncle.
Inflorescence position: Above foliage.
Number of inflorescences per lateral branch: 3–4.
Lastingness of an individual flower: 7–10 days.
Florets:
*Form.*—Cupped. As flowers mature, the florets gradually become more open/flat.
*Number per umbel.*—4–7.
*Diameter.*—76 mm on mature floret.
*Depth.*—23 mm deep on mature floret.
Petals:
*Color.*—Upper surface: The lower petals have no 'eye' present. The overall background color is Purple Group 75C, especially at edges. The lower petals have an over color that is more red going to the color of Purple Group 72C toward the center. Veining is described as Purple Group 74C. There are a few small dark veins of Purple Group 74C, but the overlaying iridescent sheen most closely matches Purple Group 72C. The upper petals have an 'eye'. They are the same color as the lower petals, except the center of the eye is Red Purple Group 64A and barely outlined with Red-Purple Group 61C. Some veining goes from Red-Purple Group 71A near the base to Red-Purple Group 64A and ends with Red-Purple Group 61B. There is also White Group 155B centrally located. Lower surface: The lower petals have a color of Purple Group 75D with veining (soft) of Red Group 64B. The lower surface of the petals with an eye have the darkest color of Red Purple Group 69A with interveinal Red Purple Group 61A and 61B.
*Shape.*—Teardrop.
*Length.*—4.2–4.9 cm.
*Width.*—3.0–4.2 cm.
*Apex shape.*—Rounded.
*Base shape.*—Tapered to a point.
*Margin.*—Entire; slightly ruffled.
*Number per floret.*—5–6.
*Texture.*—Smooth.
*Tonality from a distance.*—Lavender with Dark Red-Purple eye.
Petaloids: None present.
Pedicel:
*Length.*—4.4 cm.
*Diameter.*—0.3 cm. at attachment to floret.
*Color.*—Yellow Green 144A.
Peduncle:
*Length.*—5.5–6.0 cm.
*Diameter.*—5–7 mm.
*Texture.*—Pubescent; leathery.
*Color.*—Green Group 143A.
Sepals:
*Number.*—5.
*Pubescence.*—Present.
*Shape.*—Arrow or lance shaped.
*Width.*—2.0–5.0 mm.
*Length.*—21–23 mm.
Fragrance: The flower has no fragrance. Foliage has a 'fruity' fragrance.
Disease resistance: None observed.
Temperature tolerance: None observed.
Drought tolerance: None observed.

REPRODUCTIVE ORGANS

Stamens:
*Number* (*per flower*).—5–6.
*Filament.*—Length: 18–19 mm. Color: White Group 155 with Red-Purple Group 73B.
*Anthers.*—Shape: Elliptical. Length: 20–23 mm. Color: Red-Purple Group 59A on underside when pollen is shedding.
*Pollen.*—Color: Greyed-Orange Group 169C. Amount (generally): Average producer.
Pistils:
*Number.*—1 that separates into 5.
*Length.*—28 mm before it separates.
*Style.*—Length: 2.3 cm. Color: Red-Purple Group 59A at tips to Red-Purple Group 61C near base.
*Stigma.*—Shape: Twisted slightly, some curl downward. Color: Red-Purple Group 59A at tip. Size: 0.3 cm. high.
*Ovaries.*—Position: Superior. Pubescence: Present. Length: 0.2 cm. Width: Less than 1 mm, individually. Color: Greyed-Green Group 191A.

I claim:

1. A new and distinct variety of *geranium* plant named 'Elegance LightLavender Splash' as described and illustrated.

* * * * *

UNITED STATES PATENT AND TRADEMARK OFFICE

CERTIFICATE OF CORRECTION

PATENT NO. : PP 17,081 P2
APPLICATION NO. : 11/177685
DATED : September 5, 2006
INVENTOR(S) : Lemon It is certified that error appears in the above-identified patent and that said Letters Patent is hereby corrected as shown below:

ALL occurrences of "LightLavender" should read -- Light Lavender --

Title Page:
Item (54), Line 2 "LightLavender" should read -- Light Lavender --.
Item (50), Varietal Denomination, Line 1 "LightLavender" should read -- Light Lavender --.
Item (57), ABSTRACT, Line 1 "LightLavender" should read -- Light Lavender --.

Column 1, at Lines 2, 8, 17 and 20 "LightLavender" should read -- Light Lavender --.

Column 4, Claim 1, Line 2 "LightLavender" should read -- Light Lavender --.

Signed and Sealed this

Twenty-sixth Day of December, 2006

JON W. DUDAS
*Director of the United States Patent and Trademark Office*